(12) United States Patent
Massaro et al.

(10) Patent No.: US 10,561,127 B2
(45) Date of Patent: Feb. 18, 2020

(54) BLOOD FEEDING SYSTEM USING NONWOVEN FABRIC MATERIALS

(71) Applicant: Verily Life Sciences LLC, Mountain View, CA (US)

(72) Inventors: Peter Massaro, Belmont, CA (US); Charles Behling, Mountain View, CA (US); Tiantian Zha, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 452 days.

(21) Appl. No.: 15/260,418

(22) Filed: Sep. 9, 2016

(65) Prior Publication Data

US 2018/0070565 A1 Mar. 15, 2018

(51) Int. Cl.
*A01K 67/033* (2006.01)
*A23K 50/90* (2016.01)
*D04H 13/00* (2006.01)

(52) U.S. Cl.
CPC .......... *A01K 67/033* (2013.01); *A23K 50/90* (2016.05); *D04H 13/00* (2013.01)

(58) Field of Classification Search
CPC ...... A01K 67/033; D04H 13/00; A23K 50/90; A01N 63/00; A01M 99/00; A01M 1/023; A01M 2200/012; A01M 29/12; A01M 1/2016
See application file for complete search history.

(56) References Cited

U.S. PATENT DOCUMENTS

| | | | | |
|---|---|---|---|---|
| 4,387,849 A | * | 6/1983 | Van Loveren | A01N 25/18 239/6 |
| 4,850,305 A | | 7/1989 | Georgi et al. | |
| 4,923,119 A | * | 5/1990 | Yamamoto | A01M 1/02 239/55 |
| 4,932,155 A | * | 6/1990 | Friemel | A01N 25/18 428/198 |
| 5,074,247 A | * | 12/1991 | Gupta | A01K 1/031 119/452 |
| 5,113,799 A | * | 5/1992 | Carr | A01K 67/033 119/6.5 |
| 5,178,094 A | * | 1/1993 | Carr | A01K 67/033 119/6.5 |

(Continued)

FOREIGN PATENT DOCUMENTS

| | | |
|---|---|---|
| DE | 102007034119 | 1/2009 |
| WO | 03087322 | 10/2003 |
| WO | 2014098680 | 6/2014 |

OTHER PUBLICATIONS

International Application No. PCT/US2017/045669, "PCT Search Report", Oct. 18, 2017, 12 pages.

(Continued)

*Primary Examiner* — Joshua D Huson
(74) *Attorney, Agent, or Firm* — Kilpatrick Townsend & Stockton LLP (57) ABSTRACT

Systems and methods for a blood feeding system using nonwoven fabric materials are disclosed. In one embodiment, a feeding pouch includes: a first surface comprising an impermeable material; a second surface comprising a nonwoven fabric material, the first surface bonded to the second surface to form a pouch; and blood deposited within the pouch.

23 Claims, 5 Drawing Sheets

(56) References Cited

U.S. PATENT DOCUMENTS

| | | | | |
|---|---|---|---|---|
| 5,242,111 | A * | 9/1993 | Nakoneczny | A61L 9/127 239/44 |
| 5,359,808 | A * | 11/1994 | Fitsakis | A01M 1/2016 43/131 |
| 5,731,055 | A * | 3/1998 | Bernardo | A01N 25/18 428/480 |
| 6,162,454 | A * | 12/2000 | Ahr | A01N 25/18 424/403 |
| 6,360,477 | B1 * | 3/2002 | Flashinski | A01M 1/2044 223/86 |
| 6,534,079 | B1 * | 3/2003 | Munagavalasa | A01N 53/00 424/409 |
| 6,543,180 | B2 * | 4/2003 | Pace | A01M 29/08 43/107 |
| 6,708,445 | B1 * | 3/2004 | Israely | A01M 1/02 43/131 |
| 6,718,689 | B1 * | 4/2004 | Kolibas | A01M 1/2005 43/131 |
| 7,051,672 | B2 * | 5/2006 | Wright | A01G 1/00 119/6.5 |
| 7,988,984 | B2 * | 8/2011 | Hockaday | A01M 1/02 119/654 |
| 8,418,399 | B2 * | 4/2013 | Palencia-Adrubau | A01M 1/02 43/107 |
| 8,597,417 | B2 | 12/2013 | Kobayashi | |
| 8,802,919 | B2 * | 8/2014 | Hoffman | A01K 67/033 119/6.5 |
| 9,220,255 | B2 * | 12/2015 | Halahmi | A01M 1/2005 |
| 2003/0047142 | A1 * | 3/2003 | Cohen | A01K 67/033 119/6.5 |
| 2005/0005504 | A1 * | 1/2005 | Munagavalasa | A01N 25/18 43/129 |
| 2006/0225728 | A1 * | 10/2006 | Atkinson | A01M 1/2061 126/263.01 |
| 2009/0000180 | A1 * | 1/2009 | Palencia-Adrubau | A01M 1/02 43/131 |
| 2012/0124890 | A1 | 5/2012 | Hainze | |
| 2012/0145081 | A1 * | 6/2012 | Acar | A01K 67/033 119/6.5 |
| 2012/0151821 | A1 * | 6/2012 | Kovacs | A01M 1/02 43/107 |
| 2012/0181349 | A1 * | 7/2012 | Adleff | A01M 1/2044 239/34 |
| 2014/0209698 | A1 * | 7/2014 | Olchovy | A01M 1/2055 239/6 |
| 2016/0015019 | A1 * | 1/2016 | Olson | A01M 1/023 43/131 |
| 2016/0073622 | A1 * | 3/2016 | Jany | A01N 25/006 43/131 |
| 2016/0286782 | A1 * | 10/2016 | Manhas | A01M 1/2027 |
| 2017/0208797 | A1 * | 7/2017 | Murray | A01N 25/22 |

OTHER PUBLICATIONS

International Application No. PCT/US2017/045669, "International Preliminary Report on Patentability", Mar. 21, 2019, 9 pages.

\* cited by examiner

BLOOD FEEDING SYSTEM USING NONWOVEN FABRIC MATERIALS

BACKGROUND

Multiple facilities raise mosquitoes for research and testing purposes. Raising a large group of mosquitoes requires providing an ample food source in the form of blood. Systems for providing blood to captive mosquitoes are often expensive and inconvenient for the user. For example, some systems for blood feeding may rupture easily or clog.

SUMMARY

In one embodiment, a system of the present disclosure may comprise a feeding pouch comprising: a first surface comprising an impermeable material; a second surface comprising a nonwoven fabric material, the first surface bonded to the second surface to form a pouch; and blood deposited within the pouch.

Another embodiment of the present disclosure may comprise a blood feeding system comprising: an enclosed area for storing mosquitoes; a blood storage container comprising: a first surface comprising an impermeable material; and a second surface bonded to the first surface, the second surface comprising a nonwoven fabric material, wherein the first surface and second surface form a pouch.

In yet another embodiment, a method of the present disclosure may comprise: providing a first surface comprising a clear impermeable material; providing a second surface comprising a nonwoven fabric material; bonding the first surface to the second surface to form a pouch for storing blood; and depositing blood into the pouch.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

DETAILED DESCRIPTION

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of a Blood Feeding System Using Nonwoven Fabric Materials

In a program for rearing large numbers of blood feeding insects, e.g., mosquitoes, an ample blood feeding mechanism is required. Embodiments of the present disclosure provide a blood feeding mechanism in the form of a blood storage pouch from which the mosquitoes can consume blood. One embodiment of the present disclosure comprises a pouch comprising two types of material, an impermeable material such as plastic and a nonwoven fabric material. The impermeable material and a sheet of the nonwoven fabric material are bonded together using heat sealing, ultrasonic sealing, or an adhesive to form a pouch. The constructed pouch has an impermeable material on one side and the nonwoven fabric material on the opposite side and a shape that may approximate that of a pillowcase.

The pouch may be filled with blood for use in feeding mosquitoes. For example, the blood may be added to the pouch by either pouring pipetting the blood into an opening or valve in the pouch. Further, in some embodiments, the blood may be continuously circulated through the pouch using a circulation pump.

Further, the mosquitoes may be able to drink blood directly through the nonwoven fabric material. Thus, a single pouch may be used for both blood storage and feeding. In some embodiments, the pouch can be placed directly in a mosquito storage area (e.g., an enclosure such as a mesh, plastic, or glass enclosure), with the nonwoven fabric material exposed to the mosquitoes. Further, the nonwoven fabric material may not be air-tight, thus allowing air to pass out of the pouch, ensuring that blood is in contact with the nonwoven fabric material and therefore available to the mosquitoes. Further, in some embodiments, the impermeable side of the pouch may comprise plastic, such as a substantially clear plastic, enabling users to easily determine the quantity and state of the blood.

In some embodiments, a pouch of the present disclosure may be formed in a plurality of shapes, e.g., two surfaces pressed together like a pillowcase, a cube, a rectangular shape, a tube, or a circular shape or some other multidimensional shape, in order to fit a specific space or expand surface area available to mosquitoes for feeding. In some embodiments, scores or seams may be added to the nonwoven fabric material to further increase the amount of surface area available to the mosquitoes for feeding.

In some embodiments, multiple pouches of the present disclosure may be linked by tubes and a circulation system to ensure that a continuous supply of fresh blood is provided to the mosquitoes. Further, in some embodiments, tubes linking the pouches may be produced with nonwoven fabric material, as discussed above, thus allowing for even greater surface area for feeding.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Illustrative Systems for a Blood Feeding System Using Nonwoven Fabric Materials

Figure 1:
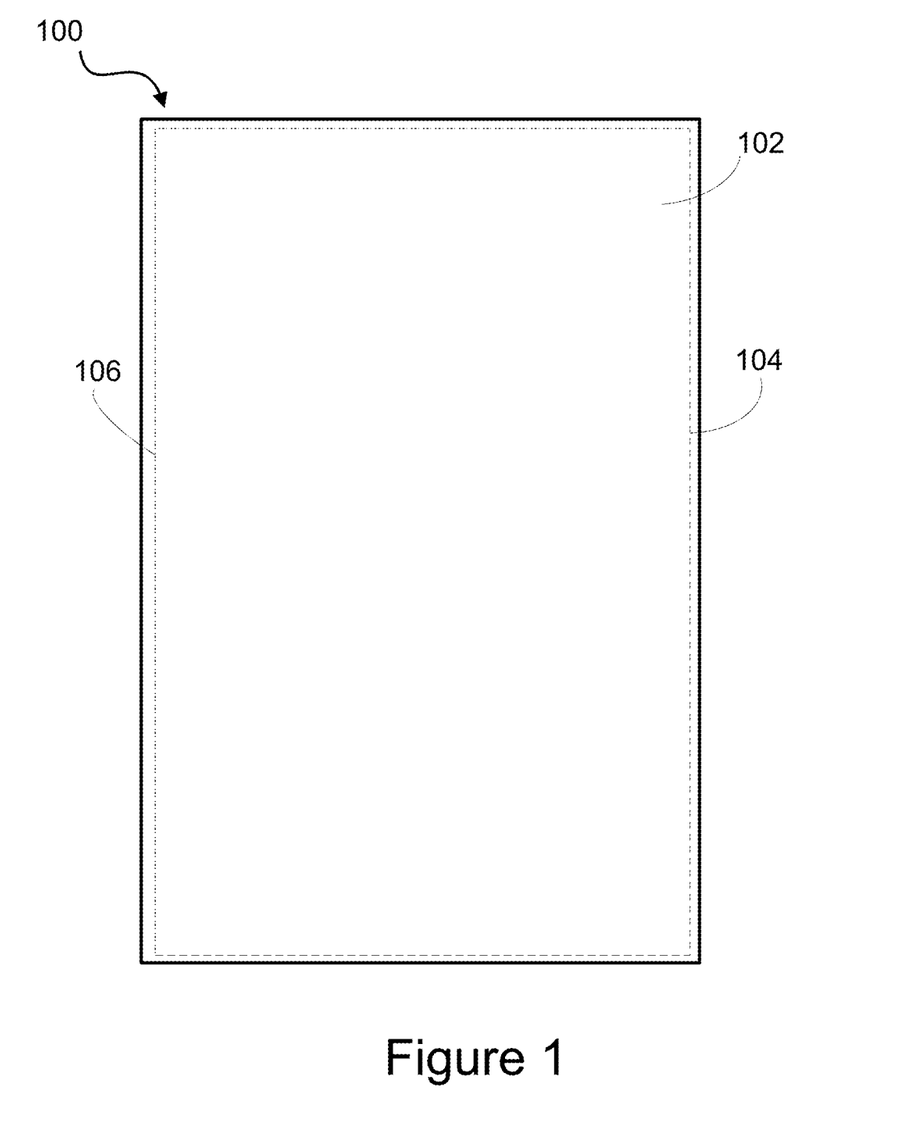
FIG. 1 shows an illustrative embodiment of a blood feeding system using nonwoven fabric materials.

FIG. 1 shows an illustrative system 100 for a blood feeding system using nonwoven fabric materials. As shown in FIG. 1, the system 100 comprises a nonwoven fabric material 102, bonded to a sheet of plastic 104, along a seam 106. The bonded nonwoven fabric material 102 and sheet of plastic 104 form a pouch for storing blood and for feeding blood to mosquitoes in a rearing program.

Nonwoven fabric material 102 provides a surface through which blood will not leak, but through which mosquitoes can consume the stored blood. Nonwoven fabric material 102 may comprise a porous hydrophobic material, for example, a spun-melt-spun (SMS) material, a melt-blown material, or a flashspun material. Examples of nonwoven fabric material 102 include: polypropylene, polyethylene, or polyester.

Plastic 104 comprises plastic through which blood will not pass. In some embodiments, plastic 104 comprises a clear plastic material, enabling the user to quickly determine the amount of blood in the pouch and whether the blood is acceptable for consumption by the mosquitoes (e.g., that the blood has not coagulated or congealed). In other embodiments, rather than a sheet of plastic, element 104 may comprise a second sheet of nonwoven fabric material. In such an embodiment, both sides of the pouch may comprise nonwoven fabric material on both sides, and may be hung inside a mosquito cage.

Seam 106 comprises a bond between nonwoven fabric material 102 and plastic 104. In some embodiments, seam 106 may be formed through bonding techniques such as heat sealing, ultrasonic sealing, or application of an adhesive.

As shown in FIG. 1, system 100 comprises the shape of a pillowcase, e.g., from two similarly sized flat surfaces, 102 and 104, bonded together along seam 106. However, in other embodiments, additional or alternative shapes may be used, e.g., to expand surface area or fit a specific area. Thus, for example, in some embodiments the system 100 may comprise, e.g., a shape approximating a cube, a rectangular shape, a tube, a circular shape, a star shape, a non-uniform shape, or some other shape. For example, in some embodiments, rather than a pouch, the system 100 may comprises a tube constructed entirely of nonwoven fabric material. Such an embodiment may maximize surface area available to mosquitoes for extracting blood. Further, in some embodiments, the nonwoven fabric material 102 may further comprises lines, scores, seams, or some other surface feature to define a flow path for the blood. Further, the lines, scores, seams, or some other surface feature may increase the amount of surface area available for mosquitoes to consume blood from the pouch.

Figure 2:
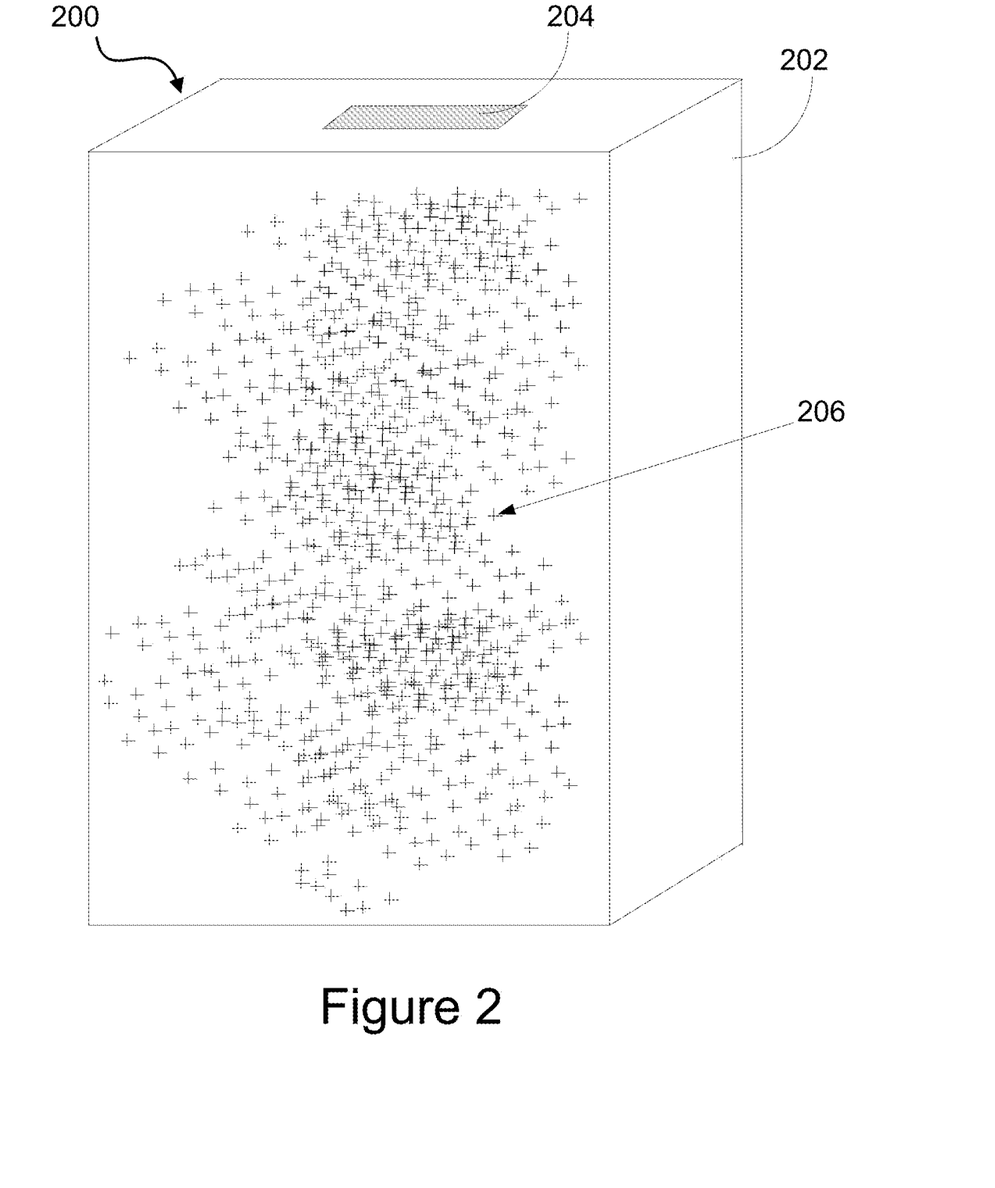
FIG. 2 shows another illustrative embodiment of a blood feeding system using nonwoven fabric materials.

Turning now to FIG. 2, which shows an example system 200 for a blood feeding system using nonwoven fabric materials according to one embodiment. As shown in FIG. 2, the system 200 comprises an enclosure 202 for containing a plurality of mosquitoes 206. The system 200 further comprises a pouch 204 comprising a nonwoven fabric side and a plastic side and is formed as described above in the discussion of FIG. 1.

As shown in FIG. 2, the plurality of mosquitoes 206 may feed from the blood stored in pouch 204. As shown in FIG. 2, the pouch 204 may be placed directly on top of enclosure 202, with the nonwoven material side of pouch 204 facing into enclosure 202 to allow mosquitoes 206 to feed on the blood. Alternatively, in some embodiments, pouch 204 may be placed inside enclosure 202 with the nonwoven fabric side facing upward to allow mosquitoes 206 to feed on the blood. Further, in some embodiments, the pouch 204 may be hung inside the enclosure 202, providing mosquitoes access to both sides of the pouch 204. In such an embodiment, both sides of the pouch may comprise a nonwoven fabric material.

As described above, the nonwoven fabric material may allow air to pass through, which may eliminate bubbles between the blood and the nonwoven fabric material. Thus, the blood in pouch 204 may stay in contact with the nonwoven fabric material regardless of positioning, allowing mosquitoes 206 to feed as long as they can get in contact with the nonwoven fabric surface.

Figure 3:
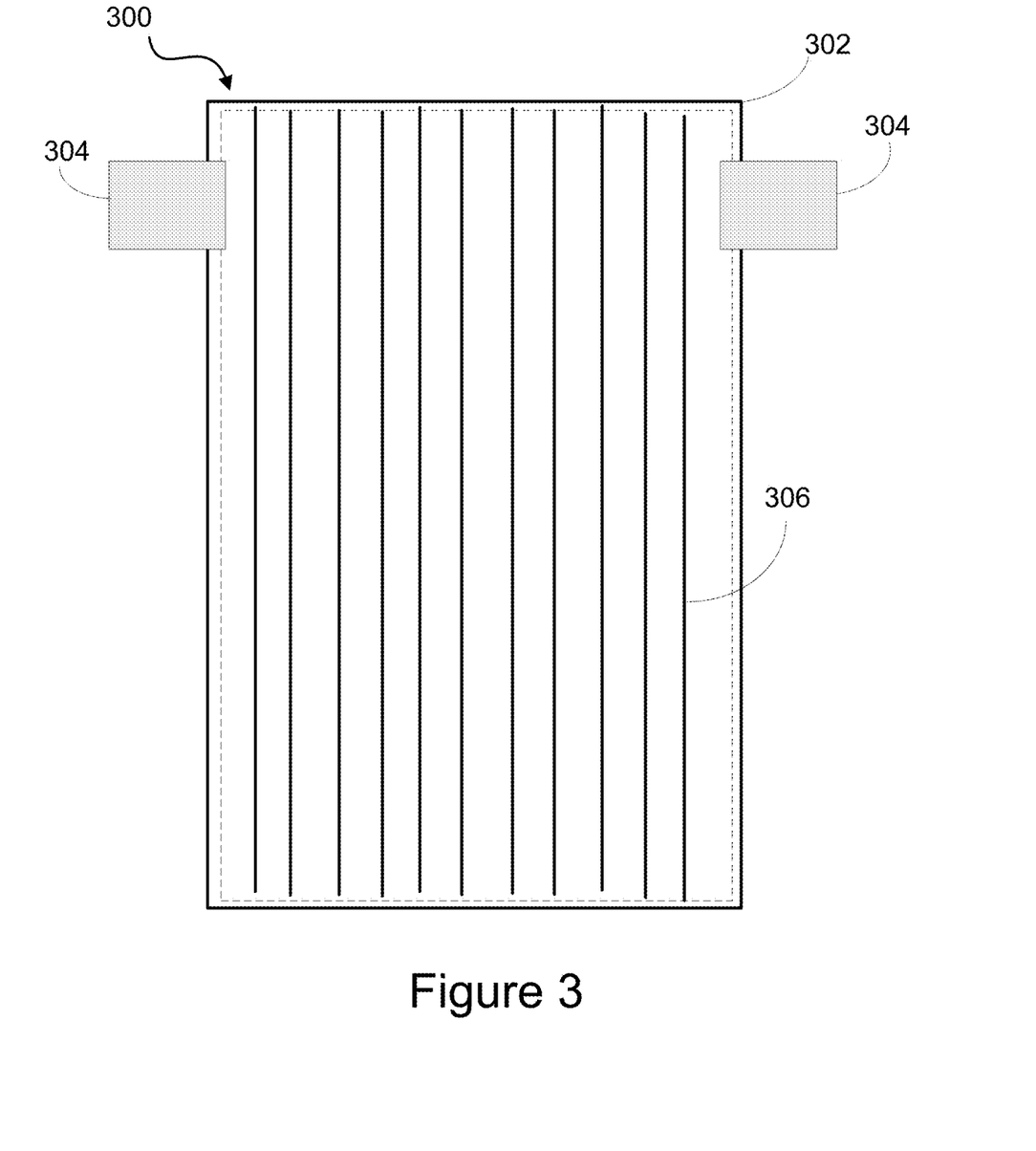
FIG. 3 shows yet another illustrative embodiment of a blood feeding system using nonwoven fabric materials.

Turning now to FIG. 3, which shows an example system 300 for a blood feeding system using nonwoven fabric materials according to one embodiment. The system 300 further comprises a pouch 302 comprising a nonwoven fabric side and a plastic side and is formed as described above in the discussion of FIG. 1. Further, as shown in FIG. 3, the pouch 302 further comprises access points 304 and scores 306. Further, in some embodiments the pouch 302 may comprise two sides that are both nonwoven fabric. In such an embodiment the pouch may be hung inside a mosquito enclosure, providing mosquitoes access to both sides of the pouch.

As shown in FIG. 3, pouch 302 comprises two access points 304. In some embodiments, access points 304 may comprise openings at the seams of the pouch 302. These openings may enable blood to be added to the pouch 302. Alternatively, in some embodiments, access points 304 comprises nozzles or valves, which are used to add or extract blood from pouch 302. In still other embodiments, access points 304 may be configured to allow pouch 302 to be coupled to a circulation system to circulate blood. In still other embodiments, access points 304 may be configured to allow multiple pouches to be coupled together to provide a larger surface area for mosquitoes to feed or to allow for a larger amount of blood to be made available to the mosquitoes.

As shown in FIG. 3, pouch 302 comprises scores 306. Scores 306 comprise thinned portions of the nonwoven fabric material that expand the surface area available to mosquitoes for feeding. Scores 306 are shown in FIG. 3 as straight lines, but in other embodiments, scores 306 may comprise any other shape, e.g., a circular shape, a serpentine shape, a star shape, or any other available shape. Further, in some embodiments scores 306 may comprise a seam or some other surface feature to expand the surface area available to the mosquitoes for feeding.

Figure 4A:
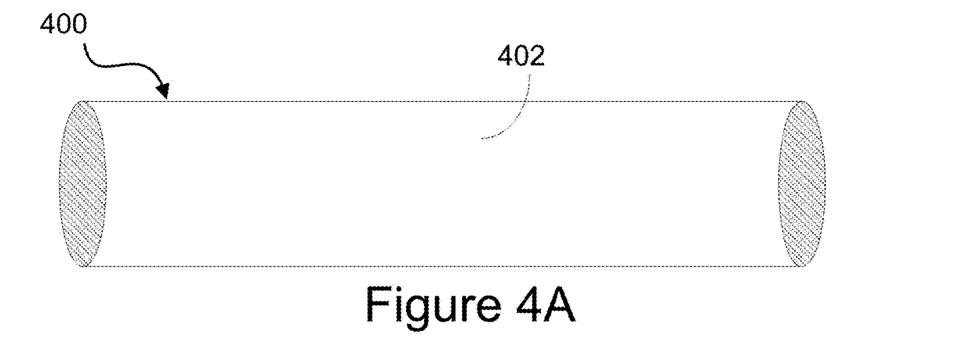
FIG. 4A shows yet another illustrative embodiment of a blood feeding system using nonwoven fabric materials.

Turning now to FIG. 4A, which shows an example system 400 for a blood feeding system using nonwoven fabric materials according to one embodiment. As shown in FIG. 4A, the system 400 comprises a tube 402. In some embodiments, tube 402 comprises a nonwoven fabric side and a plastic side and is formed as described above in the discussion of FIG. 1. Alternatively, in some embodiments, the tube 402 may comprises a tube constructed entirely of nonwoven fabric material. Such an embodiment may maximize surface area available to mosquitoes for extracting blood. As shown in FIG. 4A, tube 402 is formed in a tube or sausage shape. Such a shape may be configured to maximize available surface area, or to fit in specific spaces. Further, in some embodiments the tube may comprise a coiled or winding tube.

Figure 4B:
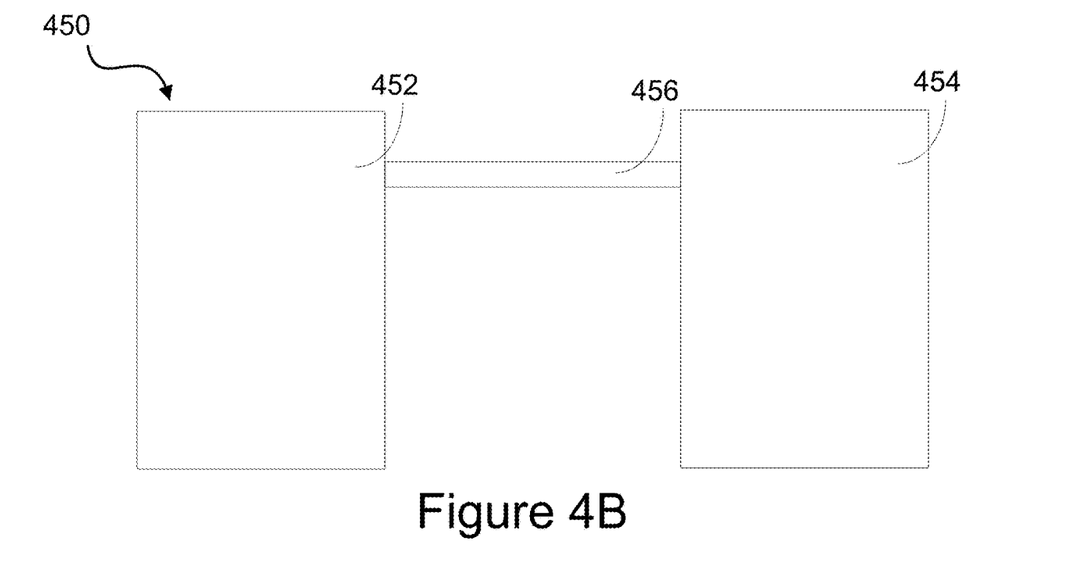
FIG. 4B shows yet another illustrative embodiment of a blood feeding system using nonwoven fabric materials.

Turning now to FIG. 4B, which shows an example system 450 for a blood feeding system using nonwoven fabric materials according to one embodiment. Pouch 452 comprises a nonwoven fabric side and a plastic side and is formed as described above in the discussion of FIG. 1. As shown in FIG. 4B, the system 450 comprises two pouches 452 and 454 each comprising a nonwoven fabric side and a plastic side and is formed as described above in the discussion of FIG. 1. Further as shown in FIG. 4B, the two pouches 452 and 454 are joined by a connecting tube 456. The configuration shown in FIG. 4B may increase surface area for mosquitoes to feed or increase the amount of available blood for the mosquitoes. Further, in some embodiments, the connecting tube 456 may comprise a nonwoven fabric material, as described in FIG. 4A above, thus further maximizing surface area.

Figure 4C:
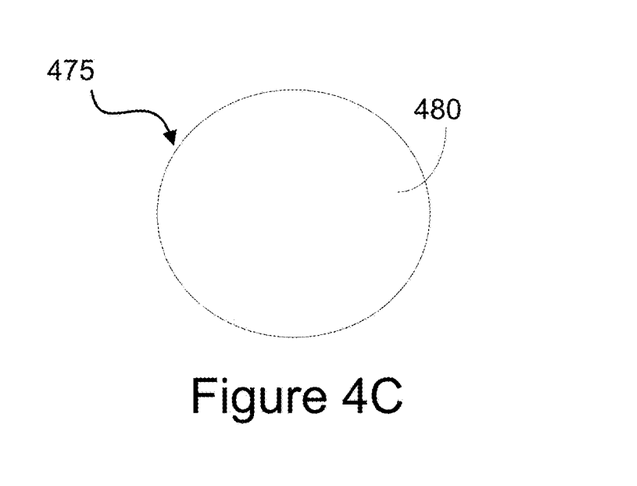
FIG. 4C shows yet another illustrative embodiment of a blood feeding system using nonwoven fabric materials.

Turning now to FIG. 4C, which shows an example system 475 for a blood feeding system using nonwoven fabric materials according to one embodiment. As shown in FIG. 4C, the system 475 comprises a pouch 480 comprising a nonwoven fabric side and a plastic side and is formed as described above in the discussion of FIG. 1. As shown in FIG. 4C, the pouch 480 has a substantially round shape.

Illustrative Methods for a Blood Feeding System Using Nonwoven Fabric Materials

Figure 5:
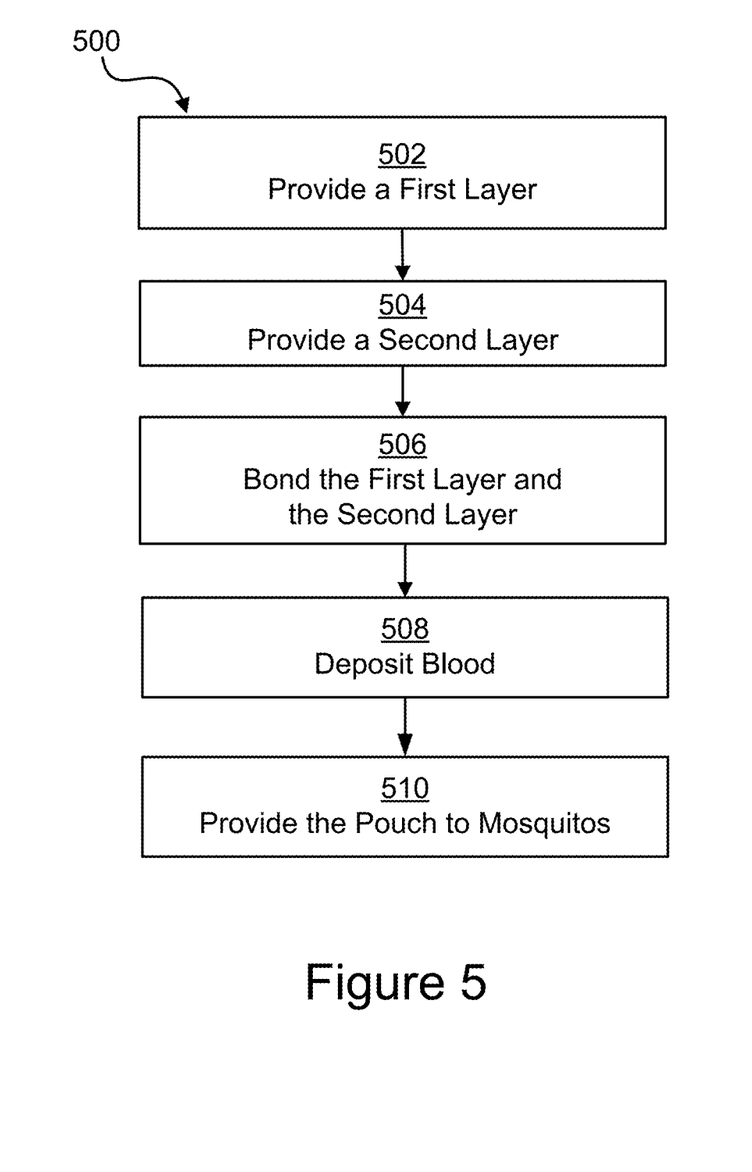
FIG. 5 shows a flow chart for steps in a method for using a blood feeding system using nonwoven fabric materials according to one embodiment.

FIG. 5 is a flow chart for a method for a blood feeding system using nonwoven fabric materials. In some embodiments the steps shown in FIG. 5 may be performed in a different order. Alternatively, in some embodiments, one or more of the steps shown in FIG. 5 may be skipped, or additional steps not shown in FIG. 5 may be performed. The steps below are described with reference to components described above with regard to system 100 shown in FIG. 1.

The method 500 begins at step 502 when a manufacturer provides a first surface 104. The first surface may comprise a plastic sheet through which blood will not pass. In some embodiments, the surface 104 comprises a clear plastic material, enabling the user to quickly determine the amount of blood in the pouch and whether the blood is acceptable for consumption by the mosquitoes (e.g., that the blood has not coagulated or congealed).

Next at step 504 a manufacturer provides a second surface 102. In some embodiments, the second surface 102 comprises a nonwoven fabric material. Nonwoven fabric material 102 provides a surface through which blood will not leak, but through which mosquitoes can consume the stored blood. Nonwoven fabric material 102 may comprise a hydrophobic material, for example, a spun-melt-spun (SMS) material, a melt-blown material, or a flashspun material. Examples of nonwoven fabric material 102 include: polypropylene, polyethylene, or polyester.

Then at step 506 the first surface and the second surface are bonded 506. The bonding may comprises bonding using techniques such as heat sealing, ultrasonic sealing, or application of one or more adhesives.

Next at step 508 blood is deposited into the pouch. The blood comprises blood for use in feeding mosquitoes, and may be heated and or treated with substances to make it transportable and appetizing to mosquitoes.

Then at step 510 the pouch is provided to mosquitoes. The pouch is provided with the nonwoven fabric surface facing toward the mosquitoes. In some embodiments the pouch may be placed directly on top of a cage for raising mosquitoes. Alternatively, in some embodiments, the pouch may be placed inside the cage.

Advantages of a Blood Feeding System Using Nonwoven Fabric Materials

There are numerous advantages of a blood feeding system using nonwoven fabric materials. For example, in some embodiments a pouch produced as described above may be both very low cost and disposable. Further, the pouch may be produced in simple shapes, e.g., by bonding two square sheets, thus reducing costs by easing manufacture.

Further, embodiments of pouches produced as described above may be highly resistant to leakage and thus are much cleaner and more convenient than other methods for feeding mosquitoes. Additionally, in some embodiments, pouches produced as described above may be air permeable and thus allow continuous contact between the blood and the nonwoven fabric material, making placement of the pouches easier. Further, some embodiments of the present disclosure provide pouches that are desirable to mosquitoes, thus increasing the success and speed of mosquito rearing programs.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A feeding pouch comprising:
a first surface comprising an impermeable material;
a second surface bonded to the first surface at bonding seams to form a pouch, the second surface comprising a nonwoven fabric material comprising one or more path seams comprising thinned areas of the nonwoven fabric material to expand surface area available for feeding, the path seams separate from the bonding seams;
one or more access points at the bonding seams; and
blood deposited within the pouch through at least one of the access points, wherein the second surface comprises a material through which the blood will not leak and through which mosquitoes can consume the blood.

2. The feeding pouch of claim 1, wherein the one or more access points further comprise a valve.

3. The feeding pouch of claim 1, wherein the impermeable material comprises a substantially clear plastic material.

4. The feeding pouch of claim 1, wherein the second surface provides a surface through which one or more insects can extract blood.

5. The feeding pouch of claim 4, wherein the one or more insects comprise one or more species of mosquitoes.

6. The feeding pouch of claim 1, wherein the first surface and the second surface are bonded in a shape approximating one of: a cube, a rectangular shape, a tube, or a circular shape.

7. The feeding pouch of claim 1, wherein the first surface is bonded to the second surface using one or more of: heat sealing, ultrasonic sealing, or an adhesive.

8. The feeding pouch of claim 1, wherein the nonwoven fabric material comprises one or more of: a hydrophobic material or a spunbond material.

9. The feeding pouch of claim 1, wherein the nonwoven fabric material comprises one or more of: a spun-melt-spun (SMS) material, a melt-blown material, or a flashspun material.

10. The feeding pouch of claim 1, wherein the nonwoven fabric material comprises one or more of: polypropylene, polyethylene, or polyester.

11. A blood feeding system comprising: an enclosed area for storing mosquitoes;
a blood storage container comprising:
a first surface comprising an impermeable material;
a second surface bonded to the first surface at bonding seams to form a pouch, the second surface comprising a nonwoven fabric material comprising one or more path seams comprising thinned areas of the nonwoven fabric material to expand surface area available for feeding, the path seams separate from the bonding seams; and
one or more access points at the bonding seams; and
blood deposited within the blood storage container, wherein the second surface comprises a material through which the blood will not leak and through which mosquitoes can consume the blood.

12. The blood feeding system of claim 11, wherein the one or more access points each comprises a valve.

13. The blood feeding system of claim 11, further comprising a plurality of pouches.

14. The blood feeding system of claim 11, further comprising a blood circulation system coupled to the pouch.

15. The blood feeding system of claim 11, wherein the impermeable material comprises a substantially clear plastic material.

16. The blood feeding system of claim 11, wherein the blood storage container is placed inside the enclosed area.

17. The blood feeding system of claim 11, wherein the blood storage container is placed in contact with the enclosed area.

18. The blood feeding system of claim 11, wherein the first surface and the second surface are bonded in shape approximating: a cube, a rectangular shape, a tube, or a circular shape.

19. The blood feeding system of claim 11, wherein the first surface is bonded to the second surface using one or more of: heat sealing, ultrasonic sealing, or an adhesive.

20. The blood feeding system of claim 11, wherein the nonwoven fabric material comprises one or more of: a hydrophobic material or a spunbond material.

21. The blood feeding system of claim 11, wherein the nonwoven fabric material comprises one or more of: a spun-melt-spun (SMS) material, a melt-blown material, or a flashspun material.

22. The blood feeding system of claim 11, wherein the nonwoven fabric material comprises one or more of: polypropylene, polyethylene, or polyester.

23. A method comprising:
providing a first surface comprising a clear impermeable material;
providing a second surface comprising a nonwoven fabric material comprising one or more path seams comprising thinned areas of the nonwoven fabric material to expand surface area available for feeding;
bonding the first surface to the second surface at bonding seams to form a pouch for storing blood, the path seams separate from the bonding seams, the pouch comprising one or more access points at the bonding seams; and
depositing blood into the pouch, wherein the second surface comprises a material through which the blood will not leak and through which mosquitoes can consume the blood.

* * * * *